(12) United States Patent
Hayes et al.

(10) Patent No.: US 10,682,778 B2
(45) Date of Patent: Jun. 16, 2020

(54) SKIN ENGAGING MEMBER COMPRISING ETHYLENE VINYL ACETATE

(71) Applicant: The Gillette Company, Boston, MA (US)

(72) Inventors: Keesha Alicia Hayes, Cambridge, MA (US); Michael John Moloney, Brimfield, MA (US); Peter Michael Ries, Cambridge, MA (US)

(73) Assignee: The Gillette Company LLC, Boston, MA (US)

( * ) Notice: Subject to any disclaimer, the term of this patent is extended or adjusted under 35 U.S.C. 154(b) by 254 days.

(21) Appl. No.: 14/944,485

(22) Filed: Nov. 18, 2015

(65) Prior Publication Data

US 2016/0143836 A1 May 26, 2016

Related U.S. Application Data

(60) Provisional application No. 62/085,071, filed on Nov. 26, 2014.

(51) Int. Cl.
| | | |
|---|---|---|
| *A61K 8/81* | (2006.01) | |
| *B26B 21/44* | (2006.01) | |
| *A61Q 9/02* | (2006.01) | |
| *A61K 8/86* | (2006.01) | |
| *C08L 71/02* | (2006.01) | |
| *C08L 23/08* | (2006.01) | |

(52) U.S. Cl.
CPC .......... *B26B 21/443* (2013.01); *A61K 8/8135* (2013.01); *A61K 8/8164* (2013.01); *A61K 8/86* (2013.01); *A61Q 9/02* (2013.01); *A61K 2800/594* (2013.01); *A61K 2800/87* (2013.01); *C08L 23/0853* (2013.01); *C08L 71/02* (2013.01)

(58) Field of Classification Search
None
See application file for complete search history.

(56) References Cited

U.S. PATENT DOCUMENTS

| | | | |
|---|---|---|---|
| 5,134,775 A | | 8/1992 | Althaus et al. |
| 5,349,750 A | * | 9/1994 | Tseng .................. A61K 8/8135 30/32 |
| 5,454,164 A | | 10/1995 | Yin et al. |
| 5,551,152 A | * | 9/1996 | Tseng .................. A61K 8/8135 30/32 |
| 5,711,076 A | | 1/1998 | Yin et al. |
| 6,298,558 B1 | | 10/2001 | Tseng et al. |
| 6,301,785 B1 | | 10/2001 | Kwiecien et al. |
| 7,121,754 B2 | | 10/2006 | Bressler et al. |
| 9,106,038 B2 | | 8/2015 | Telfort et al. |
| 2004/0177513 A1 | * | 9/2004 | Vreeland ............... B26B 21/443 30/133 |
| 2004/0181943 A1 | | 9/2004 | Kwiecien |
| 2006/0225285 A1 | | 10/2006 | Shavtcheff et al. |
| 2006/0272155 A1 | | 12/2006 | Mehta et al. |
| 2008/0060201 A1 | | 3/2008 | Kwiecien |
| 2009/0223057 A1 | | 9/2009 | Coope Epstein et al. |
| 2012/0094006 A1 | | 4/2012 | Kwiecien |

* cited by examiner

*Primary Examiner* — Dominic Lazaro
(74) *Attorney, Agent, or Firm* — Kevin C. Johnson (57) ABSTRACT

A skin engaging member suitable for use in a hair removal device, said skin engaging member comprising ethyl vinyl acetate having a low level of vinyl acetate and a water soluble polymer.

12 Claims, 1 Drawing Sheet

SKIN ENGAGING MEMBER COMPRISING ETHYLENE VINYL ACETATE

BACKGROUND OF THE INVENTION

Many razor cartridges include shaving aids, commonly referred to as lubrication strips. These lubrication strips are typically present behind the blades in an aft position such that as a user performs a shave stroke, the skin is contact by the blades prior to contact by the shaving aid. Many different types of shaving aids have been disclosed. See e.g., U.S. Pat. Nos. 7,121,754; 6,298,558; 5,711,076; 5,134,775; 6,301,785; U.S. Patent Publ. Nos. 2009/0223057, 2004/181943, 2006/0225285, and 2006/0272155, 2008/060201A1; and WO 2011/047211. Some shaving aids contain one or more types of polyethylene oxide (PEO) with water insoluble polymers such as polystyrene.

One problem with the use of polystyrene is that it requires high processing temperatures during extrusion. The high processing temperatures can adversely impact the integrity of chemicals in the shaving aids potentially degrading them which can possibly impact consumer experience during use or product life cycle. The processing conditions required when using polystyrene can also limit what ingredients can be incorporated into the shaving aid as certain materials cannot be subjected to such temperatures or processing conditions.

Use of ethylene vinyl acetate as a water insoluble polymer has also been suggested. See e.g. U.S. Pat. Nos. 5,349,750, 5,454,164, and 5,551,152. Though ethylene vinyl acetate has been generally described as a potential water insoluble polymer for use in a shaving aid, many factors, including level of ingredients, grade of ethylene vinyl acetate, and processing conditions can impact the suitability of the shaving aid for actual use. U.S. Pat. No. 5,551,152, for example mentions shaving aid composites which can have 10-50% ethylene vinyl acetate and 50-90% of shaving aid material, with commercial grades of vinyl acetate ranging in vinyl acetate content from 5-50% by weight. This reference goes on to provide several examples of shaving aids with vinyl acetate having vinyl acetate content at 25% (Elvax 360).

Despite the earlier attempts, there remains a need for shaving aids that provide the right amount of lubrication and consistent lubrication over multiple uses where the product retains a sufficient effective lifespan (which can include structural integrity and/or ability of the shaving aid to continue providing a certain degree of lubrication after multiple uses). This is a significant challenge given shaving conditions vary by user based on individual shaving habit and environmental conditions; when designing products that are robust and can provide desirable lubrication yet retain structural integrity over multi-uses (in some instances up to 6 shaves, even as much as 12 shaves).

As such, there remains a need for a new shaving aid which can be processed at a wider range of operating conditions, particularly when considering extrusion type methods but still provide desirable lubrication over the life of the product. These and other benefits may be addressed by one or more embodiments of the following invention.

SUMMARY OF THE INVENTION

One aspect of this invention relates to a skin engaging member, suitable for use with a hair removal device, such as a razor or depilatory and scraping tool, said skin engaging member comprising a water soluble polymer and a non-water soluble polymer comprising ethylene vinyl acetate. This skin engaging member can be used on a hair removal device such as a razor.

The skin engaging member comprises ethylene vinyl acetate having a vinyl acetate % of about 18% or less. In one embodiment, the skin engaging member has a total vinyl acetate level of from about 0.2% up to 7.5%, by weight of the skin engaging member, preferably from about 0.4% to about 5.75%. In one embodiment the skin engaging member comprises about 50% to about 78% of a water-soluble polymer; and about 20% to about 40% of ethylene vinyl acetate by weight of the skin engaging member, preferably from about 26% to about 32%, said ethylene vinyl acetate having a vinyl acetate % of less than 18%.

Another aspect of the invention relates to a method of making such a skin engaging member.

DETAILED DESCRIPTION OF THE INVENTION

I. Skin Engaging Member

The skin engaging member of the present invention is suitable for use on a hair removal device (such as a razor), said skin engaging member consists of one or more layers of a shaving aid material, which can be of a polymeric material. Multi-layered skin engaging member systems such as those described in U.S. Pat. No. 5,956,848. The skin engaging member can also be made of multiple adjacent strips such as disclosed in U.S. Pat. No. 6,298,559. The skin engaging member comprises at least one shaving aid. The shaving aids of the present invention are formed of a polymeric matrix comprising a water soluble polymer and a water-insoluble polymer comprising ethylene vinyl acetate (EVA).

The water-insoluble polymer material can be at a level of from about 22% to about 40%, preferably about 26% to about 40%, of EVA by weight of the skin engaging member. The amount of EVA can also be selected at a level of from about 25% to about 32%, or from about 26% to about 30%. Though higher levels of EVA have been disclosed, having too much EVA (in effect too much water-insoluble polymer) can impact the amount of lubrication and other potential benefits provided by the skin engaging member because it can reduce the amount of other ingredients and water-soluble polymer that can be provided. The EVA can be added as a raw material feed on its own, or can be introduced with other ingredients. For purposes of this invention, the level of EVA refers to total amount of EVA in the skin engaging member regardless of how it is introduced. EVA can be introduced pre-mixed/combined with other ingredients (actives or fillers), or can be combined during mixing steps.

In one embodiment, the EVA is selected to have a % vinyl acetate (% VA) of about 18% or less, possibly less than about 18%, including less than about 12%. In one embodiment the % vinyl acetate can be, as low as about 2% to about 5%, preferably from about 2.5% to 4%. The % vinyl acetate can also be selected at a level of from about 8% to about 15%, or from about 10% to about 13%. "About" as used herein with regards to EVA level and % vinyl acetate can mean±0.1%. Without intending to be bound by theory, it is believed that selecting a grade of EVA with a % vinyl acetate as specified herein provides a matrix material that provides enough structural integrity without limiting the ability of the skin engaging member to provide lubrication over multiple uses. It is believed that a % vinyl acetate can impact the structural integrity benefits provided by the EVA. It is believed that high total amounts of vinyl acetate (which is a function of level of EVA and the % vinyl acetate) can cause the skin engaging member to swell or deform excessively or too early in its lifespan.

In one embodiment, the shaving aid comprises a total vinyl acetate level of from about 0.2 up to 7.5%, by weight of the skin engaging member, preferably from about 0.4 to about 5.75%. The total vinyl acetate is determined on a total basis including any vinyl acetate that is present in the skin engaging member, whether it comes from the ethylene vinyl acetate or another feed, such as the colorant. The total vinyl acetate level can also be from about 0.55 to about 4.3%, or from about 0.75 to about 3%, preferably less than about 1.5%. The total vinyl acetate level would be inclusive of the vinyl acetate present in the skin engaging member from EVA or from other sources based on the weight of the skin engaging member. Those of skill in the art will understand that any carrier or other non-active tray or support would not be considered in determining total vinyl acetate level.

Without intending to be bound by theory, it is believe when formulating with an EVA having VA % 18%, it can be preferred to have more EVA present so that the total VA % is from about 4% to about 7.2%, by weight of the skin engaging member. Further, if using an EVA having a 12% VA, it can be preferred to control the EVA levels to have a total VA % from about 2.6 to about 4.8%. Furthermore, if using an EVA having a 9% VA it can be preferred to have a total VA % from about 2.0 to about 3.6%. If using an EVA with a grade of 2.5% VA it can be preferred to have a total VA % from about 0.5 to about 1%.

Without intending to be bound by theory, it is now believed that as % VA increases, the material can become more elastic, less stiff. Though this was seen as an advantage, such as pointed out in U.S. Pat. No. 5,349,750 at col. 2, first paragraph, stating "Increasing the amount of vinyl acetate in an ethylene vinyl acetate copolymer reduces its crystallinity, increases its flexibility, and reduces its hardness. Despite this teaching it has now been found that having high levels of vinyl acetate, such as 18% or above can have undesirable benefits from this increased flexibility and reduced hardness. Without intending to be bound by theory, it is now believed that use of vinyl acetate with a % VA of higher than 18%, such as EVA with 25% VA grade can result in greater challenge to mechanically retain in a cartridge. It is believed that this can become even more challenging with higher MW PEO grades, which are known to potentially cause swelling of the water soluble matrix, but also provide desirable lubrication. By using lower % VA grades as described herein, it is believed that a less elastic skin engaging member can be formulated, which enables managing the greater swelling forces of high MW PEO, and/or permits a lower total level of insoluble matrix material.

% VA can be determined on an "as added" basis based on a total material basis of the feed streams. For determining % VA from product post manufacturing, % VA can be measured with many different measurement technologies that are available for compositional analysis. The total amount of insoluble matrix material can be determined by a gravimetric comparison of a completely leached and dried lubricating member with the starting mass. The % VA in the insoluble matrix can be measured by quantitative FTIR spectroscopy such as described by Williams (*J. Chem. Educ.*, 1994, 71 (8), p A195), or by nuclear magnetic resonance to determine relative spectral peak areas to determine the proportion of vinyl acetate present in the skin engaging member as described by Koopmans et. al. (J. Adhesion, 1983, Vol. 15, pp. 117-124). In one embodiment, the % VA is determined on an "as added" basis. In another embodiment, the % VA is determined post production. Those of ordinary skill in the art will understand that % VA should be the same between an "as added" basis and if analyzed post production with minor potential variations plus or minus up to 0.1%, based on analytical method error, potential volatilization of ingredients and other processing factors.

Without intending to be bound by theory it is believed that skin engaging members in accordance with the present invention provides one or more of the following benefits.

In one embodiment, the skin engaging member provides noticeable lubrication benefits to a meaningful segment of users compared to conventional shaving aids known in the art, such as shaving aids using high impact polystyrene as a water-insoluble polymer with the same amount and type of water soluble polymer.

In another embodiment, the skin engaging member has improved mechanical integrity compared to other shaving aids. Mechanical Integrity, as defined here, can mean that the skin engaging member has minimal to no visually notable defects after 8 normal shaves in-use. Defects can include the skin engaging member curling or lifting at the edges, shrinking along its longest length, excessive increase (swelling) in skin engaging member thickness, bulge out of the cartridge, or other physical defects that can have undesirable functional or aesthetic impacts.

Another potentially useful water-insoluble polymer is polystyrene, preferably a general purpose polystyrene or a high impact polystyrene (HIPS) such as Styrenics 5410 from Ineos (i.e. polystyrene-butadiene), such as BASF 495F KG21.

The strip or any portion should contain a sufficient quantity of water-insoluble polymer to provide adequate mechanical strength, both during production and use. Without intending to be bound by theory, it is believed that EVA provides superior toughness and resiliency to HIPS evidenced by slower matrix wear when subjected to abrasion. It is also believed that EVA also allows for lower extrusion and molding process temperatures than HIPS. In one embodiment, the matrix does not include any other water-insoluble polymers other than EVA. In one embodiment, the matrix is free or essentially free (meaning no amount of said ingredient is intentionally added but could be present at trace levels as processing carryover) of polystyrene. In another embodiment, however, EVA can be blended with HIPS or another water-insoluble polymer of blends thereof.

Without intending to be bound by theory, it is believed that the use of EVA in the present invention allows for a lowered extrusion process temperature, for example skin engaging members comprising EVA could be extruded at 120° C., for some formulations even as low as 100 C, compared to skin engaging members comprising high impact polystyrene would could require temperatures around 180° C. This processing flexibility can enable previously unavailable ingredients to be included as they may be able to withstand the lower processing temperatures.

In one embodiment, the skin engaging member comprises a solid polymeric matrix having a melting temperature from about 95° C. to about 205° C., said matrix comprising a water-insoluble polymer material comprising ethylene vinyl acetate and combined with a water-soluble polymer material and other optional adjunct or secondary ingredients.

Additional water-insoluble polymers can also be used, in addition to the EVA. Examples of additional water-insoluble polymers include those known in the art and used in skin engaging members found on razors today. Specific water-insoluble polymers which can be used include polyethylene (PE), polypropylene, polystyrene (PS), butadiene-styrene copolymer (e.g. medium and high impact polystyrene), polyacetal, acrylonitrile-butadiene-styrene copolymer, ethylene vinyl acetate copolymer, polyurethane, and blends thereof, such as polypropylene/polystyrene blend or polystyrene/impact polystyrene blend. These matrix polymers can also be free or essentially free of one of more of these additional water-insoluble polymers.

Suitable water soluble polymers which can be used in accordance with the present invention include, but are not limited to, one or more of: a polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, silicone polymers, and mixtures thereof. In one embodiment, said water soluble polymer is selected from the group consisting of polyethylene oxide, polyethylene glycol, and a mixture thereof.

In one embodiment, the skin engaging member comprises any other ingredients commonly found in commercially available skin engaging members, such as those used on razor cartridges by Gillette, Schick or BIC. Non-limiting examples of such skin engaging members include those disclosed in U.S. Pat. Nos. 6,301,785, 6,442,839, 6,298,558, 6,302,785, and U.S Patent Pubs 2008/060201, and 2009/0223057. In one embodiment, the skin engaging member further comprises a skin engaging member ingredient selected from the group consisting of polyethylene oxide, polyvinyl pyrrolidone, polyacrylamide, hydroxypropyl cellulose, polyvinyl imidazoline, polyethylene glycol, poly vinyl alcohol, polyhydroxyethylmethacrylate, silicone copolymers, sucrose stearate, vitamin E, soaps, surfactants, panthenol, aloe, plasticizers, such as polyethylene glycol; beard softeners; additional lubricants, such as silicone oil, Teflon® polytetrafluoroethylene powders (manufactured by DuPont), and waxes; essential oils such as menthol, camphor, eugenol, eucalyptol, safrol and methyl salicylate; tackifiers such as Hercules Regalrez 1094 and 1126; non-volatile cooling agents, inclusion complexes of skin-soothing agents with cyclodextrins; fragrances; antipruritic/counterirritant materials; antimicrobial/keratolytic materials such as Resorcinol; anti-inflammatory agents such as Candilla wax and glycyrrhetinic acid; astringents such as zinc sulfate; surfactants such as pluronic and iconol materials; compatibilizers such as styrene-b-EO copolymers; mineral oil, polycaprolactone (PCL), and combinations thereof.

Without intending to be bound by theory, it is believed that many potentially useful ingredients can be adversely impacted by conventional shaving aid extrusion and molding processing conditions. For example, shaving aids comprising polystyrene could require high temperatures or high pressures for extrusion. These conditions can result in outright or premature decomposition or decrease in efficacy of these ingredients. In one embodiment, the shaving aid is made at a controlled temperature such as below 130° C.

The water-soluble polymer will preferably comprise at least 50%, more preferably at least 60%, by weight of the skin engaging member, up to about 78%, or up to about 70% of the matrix. The more preferred water soluble polymers are the polyethylene oxides generally known as POLYOX (available from Dow or ALKOX (available from Meisei Chemical Works, Kyoto, Japan). These polyethylene oxides will preferably have mol·wt·s of about 100,000 Da to 10 million, most preferably about 300,000 Da to 6 million The water-soluble polymeric matrix of the present invention comprises a mixture of high mol wt PEO and low mol wt PEO. The relative amounts of high and low mol wt PEO can respectively be: from about 63.5% to about 95% by weight of the mixture of high and low weight PEO, of a high mol wt PEO, or from about 65% to about 90%, or from about 70% to about 75%; and from about 5% to about 36.5% by weight of the mixture of high and low weight PEO, of a low mol wt PEO, or from about 10% to about 35%, or from about 25% to about 30%. In one embodiment, the high and low mol wt PEO consists essentially of said amounts of high mol wt PEO and low mol wt PEO. Other polymers can also be present aside from the high and low mol wt PEO mixture.

In one embodiment, the mixture of PEO has a high mol wt PEO to low mol wt PEO ratio of about 1.75:1 to about 19:1, or from about 1.8:1 to about 10:1. In one embodiment, the ratio is greater than 1.8:1. Without intending to be bound by theory, it is believed that such a ratio, of more high mol wt PEO to low mol wt PEO, compared what has been disclosed, provides improved benefits to the user during the shave, such as improved lubrication and glide over skin during the shaving stroke. Without intending to be bound by theory, it is believed that this can provide a more comfortable and pleasurable shaving experience by decreasing friction on skin and other related irritations. In addition, it is believed that formulating at lower processing temperatures can reduce the molecular weight degradation of the PEO starting materials, and increase the mol wt. delivered during shaving. This has the additional benefit of reducing the overall level of PEO needed, in turn enabling higher levels of other materials that can be included without a compromise in shaving comfort. Other ingredients which are temperature sensitive, such as fragrance and other skin conditioners and cosmetic agents, can also benefit from extruding at lower temperatures.

As defined here, a high mol wt PEO has an average mol wt of about 2 million to 10 million Da, preferably of about 5 million Da. Commercially available sources of high mol wt PEO include POLYOX COAGULANT ("COAG"). Also, as defined herein, a low mol wt PEO has an average mol wt of less than 1 million to about 100,000 Da, preferably of about 300,000 Da. Commercially available sources of low mol wt PEO include POLYOX WSR-N-750 ("N750"). Another commercially available type of PEO is Polyox WSR 308.

In one embodiment, the mixture of high and low mol wt PEO is at a level of from about 20% to about 100% of the skin engaging member, or from about 35% to about 90%, or from about 50% to about 90%, or 75% to about 80%.

In one embodiment, the matrix comprises more PEO than EVA.

Figure 2:
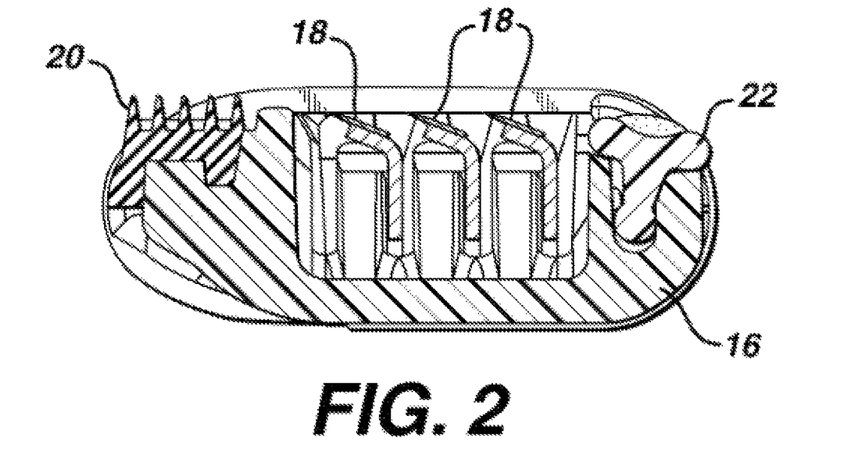
FIG. 2 is a sectional view taken along line 2-2 of FIG. 1.

In one embodiment, the skin engaging member comprises more than one layer, or a base layer and a second layer at least partially coating a portion of said base layer, such as shown in FIG. 2 where skin engaging member 22 has two layers. The mixture of the high and low mol wt PEO can be present in either or both layers. Skin engaging members having more than two layers are also within the scope of the present invention.

The skin engaging member of the present invention can be a single uniform composition, or can be formed of more than one layer. In one embodiment, the skin engaging member comprises at least two layers, a top layer and a base layer. In one embodiment, the top layer can have a ratio of water soluble polymers (i.e. PEO) to water insoluble polymers (i.e. EVA) of from about 3:1 to 1:1 by weight. In one embodiment, the base layer can have a ratio of such components of from about 5:4 to about 1:1. In one embodiment, the proportion of water soluble polymers to insoluble polymers in the first layer is higher than a comparable ratio in the second layer.

Furthermore, the skin engaging member can include a sheath and core such as disclosed in U.S. Pat. No. 6,298,558 or 7,581,318, wherein the present mixture comprising PEO and EVA can be used as the sheath or core, preferably as the core with the sheath being made of a non-soluble polymer material such as a thermoplastic resin including but not limited to water insoluble polymers like high impact polystyrene, polystyrene, ethylene vinyl acetate, and mixtures thereof, as well as water soluble polymers such as those disclosed herein. In one embodiment, the core can be referred to as the first layer and the sheath as the second layer. In one embodiment, the sheath can comprise the mixture of PEO and EVA of the present invention, or a non active sheath that does not disperse, dissolve or otherwise release active lubricants during use. In such as case, the sheath would not be considered in determining the weight % of the skin engaging member.

It should be understood that other types of PEO may also be included aside from the high and low mol wt PEOs described above (i.e. PEOs of mol wt above 10 million, between 1 million and 2 million, and/or below 100,000 Da). Those of skill in the art will understand that if PEOs outside these ranges of high and low mol wt PEO are included, the relative ratio of high mol wt PEO to low mol wt PEO will stay the same but the overall level of each of these PEOs can decrease as other ingredients are added to the shaving aid. The polyethylene oxide blend may also contain up to about 10% by weight of a lower mol wt PEO (i.e. MW<10,000) polyethylene glycol such as PEG-100.

Other optional water soluble or insoluble polymers can also be included in the matrix. In one embodiment, the matrix further comprises from about 0.5% to about 50%, preferably from about 1% to about 20%, polycaprolactone (preferably mol·wt. of 30,000 to 60,000 daltons). See U.S. Pat. No. 6,302,785.

In another embodiment, the skin engaging member may contain other conventional skin engaging member ingredients, such as low mol·wt. water-soluble release enhancing agents such as polyethylene glycol (MW<10,000, e.g., 1-10% by weight PEG-100), water-swellable release enhancing agents such as cross-linked polyacrylics (e.g., 2-7% by weight), colorants, antioxidants, preservatives, vitamin E, aloe, cooling agents, essential oils, beard softeners, astringents, medicinal agents, etc. Portions that contain a colorant can be designed to release the colorant (e.g., by leaching or abrasion), and thereby cause the strip to change color during shaving, preferably in response to wear of the colored portion, so as to provide an indication to the user that the skin engaging member and/or the razor cartridge has reached the end of its effective life or the end of its optimum performance. A portion may contain, for example, between about 0.1% and about 5.0% (preferably between about 0.5% and 3%) colorant by weight.

II. Skin Care Actives

Various skin care actives ("actives") which are commonly used for topical application can also used in the skin engaging member as a neat product and/or in an encapsulate, or as a coating. Various actives suitable for cosmetic and dermatological use can be used herein. Non-limiting examples of suitable actives include one or more of: Bisabolol and ginger extract, a surfactant derived from olive oil such as Olivem 450® and Olivem 460®, Lauryl p-Cresol Ketoxime, 4-(1-Phenylethyl)1,3-benzenediol, Lupin (*Lupinus albus*) oil & wheat (*Triticum vulgare*) germ oil unsaponifiables, Hydrolyzed lupin protein, Extract of L-lysine and L-arginine peptides, Oil soluble vitamin C, Evodia rutaecarpa fruit extract, Zinc pidolate and zinc PCA, Alpha-linoleic acid, p-thymol, and combinations thereof; at least one additional skin and/or hair care active selected from the group consisting of sugar amines, vitamin $B_3$, retinoids, hydroquinone, peptides, farnesol, phytosterol, dialkanoyl hydroxyproline, hexamidine, salicylic acid, N-acyl amino acid compounds, sunscreen actives, water soluble vitamins, oil soluble vitamins, hesperedin, mustard seed extract, glycyrrhizic acid, glycyrrhetinic acid, carnosine, Butylated Hydroxytoluene (BHT) and Butylated Hydroxyanisole (BHA), menthyl anthranilate, cetyl pyridinium chloride, tetrahydrocurmin, vanillin or its derivatives, ergothioneine, melanostatine, sterol esters, idebenone, dehydroacetic acid, Licohalcone A, creatine, creatinine, feverfew extract, yeast extract (e.g., Pitera®), beta glucans, alpha glucans, diethylhexyl syringylidene malonate, erythritol, p-cymen-7-ol, benzyl phenylacetate, 4-(4-methoxyphenyl)butan-2-one, ethoxyquin, tannic acid, gallic acid, octadecenedioic acid, p-cymen-5-ol, methyl sulfonyl methane, an avenathramide compound, fatty acids (especially poly-unsaturated fatty acids), anti-fungal agents, thiol compounds (e.g., N-acetyl cysteine, glutathione, thioglycolate), other vitamins (vitamin B 12), beta-carotene, ubiquinone, amino acids, their salts, their derivatives, their precursors, and/or combinations thereof; and a dermatologically acceptable carrier. These and other potentially suitable actives are described in greater detail in U.S. Patent Publication No. 2008/0069784.

Additional actives that can be used include those commercially available under the following tradenames: Signaline S, Jojoba Oil, Ceramidone, Net DG, Pal-GHK (Paltenex), Rhodysterol, Vital ET, and combinations thereof.

In another embodiment, the active can be a methyl naphthalenyl ketone. The methyl naphthalenyl ketone can be a 1-(1,2,3,4,5,6,7,8-octahydro-2,3,8,8-tetramethyl-2naphthalenyl)-ethan-1-one molecule or an isomer or derivative thereof. Commercially available as Iso-E-Super from IFF of New York. Other sensates can also be used, including those which have ability to up-regulate the TRPM8 receptor, which has been described as the cool menthol receptor. Non-limiting examples of suitable TRPM8 regulators include: p-methane-3,8-diol; Isopulegol; Menthoxypropane-1,2,-diol; Curcumin; Menthyl Lactate; Gingerol; Icilin; Menthol; Tea Tree Oil; Methyl Salicylate; Camphor; Peppermint Oil; N-Ethyl-p-menthane-3-carboxamide; Ethyl 3-(p-menthane-3-carboxamido)acetate; 2-Isopropyl-N,2,3-trimethylbutyramide; Menthone glycerol ketal, and mixtures thereof.

The active ingredient can also be one or more skin care actives suitable for topical use. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. The 11$^{th}$ edition of PCPC's International Cosmetic Ingredient Dictionary and Handbook, along with the 2005 PCPC International Buyer's Guide both provide useful compositions which may be suitable for incorporation into the skin engaging member of the present invention. Examples of these ingredient classes include: abrasives, absorbents, aesthetic components such as fragrances, pigments, colorings/colorants, essential oils, skin sensates, astringents, etc. (e.g., clove oil, camphor, eucalyptus oil, eugenol, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, fatty alcohols and fatty acids, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents, skin-conditioning agents, skin soothing and/or healing agents and derivatives, skin treating agents, thickeners, and vitamins and derivatives thereof.

Additional non-limiting examples of additional suitable skin treatment actives are included in U.S. 2003/0082219 in Section I (i.e. hexamidine, zinc oxide, and niacinamide); U.S. Pat. No. 5,665,339 at Section D (i.e. coolants, skin conditioning agents, sunscreens and pigments, and medicaments); and US 2005/0019356 (i.e. desquamation actives, anti-acne actives, chelators, flavonoids, and antimicrobial and antifungal actives). It should be noted, however, that many materials may provide more than one benefit, or operate via more than one mode of action. Therefore, classifications herein are made for the sake of convenience and are not intended to limit the active to that particular application or applications listed.

a. Cooling Agents

Non-limiting examples of suitable cooling agents include: L-menthol; p-methane-3,8-diol; Isopulegol; Menthoxypropane-1,2,-diol; Curcumin; Menthyl Lactate (such as Frescolat ML by Symrise); Gingerol; Icilin; Tea Tree Oil; Methyl Salicylate; Camphor; Peppermint Oil; N-Ethyl-p-menthane-3-carboxamide; Ethyl 3-(p-menthane-3-carboxamido)acetate; 2-Isopropyl-N,2,3-trimethylbutyramide; Menthone glycerol ketal, Menthone Glyerine Acetal; Coolact 10; and mixtures thereof. These and other cooling agents are known and described in various publications, such as U.S. Patent No. 2008/0300314A1, U.S. Pat. Nos. 5,451,404 and 7,482,373. In yet another embodiment, the cooling agent comprises one or more of the cooling agents previously described for use in various shave aids. See e.g., U.S. Pat. Nos. 5,095,619; 5,713,131; 5,095,619; 5,653,971; 6,298,558; 6,944,952; and 6,295,733.

In one embodiment, the skin engaging member further comprises one or more cooling agents. It is now well established that sensations such as cool or cold can be attributed to activation of receptors at peripheral nerve fibers by a stimulus such as low temperature or a chemical coolant, which produces electrochemical signals that travel to the brain, which then interprets, organizes and integrates the incoming signal(s) into a perception or sensation. Different classes of receptors have been implicated in sensing cold temperatures or chemical coolant stimuli at mammalian sensory nerve fibers. Among these receptors, a major candidate involved in sensing cold has been identified and designated as cold- and menthol-sensitive receptor (CMR1) or TRPM8. The TRPM8 nomenclature for the receptor comes from its characterization as a non-selective cation channel of the transient receptor potential (TRP) family that is activated by stimuli including low temperatures, menthol and other chemical coolants. However, the precise mechanisms underlying the perception of a pleasant cooling sensation on skin or oral surfaces are presently not clearly understood. While it has been demonstrated that the TRPM8 receptor is activated by menthol and other coolants, it is not fully understood what other receptors may be involved and to what extent these receptors need to be stimulated or perhaps suppressed in order that the overall perceived sensation would be pleasant, cooling and refreshing.

For example, menthol is widely used as a cooling agent, but menthol can also produce other sensations including tingling, burning, prickling and stinging as well as a minty smell and bitter taste. Thus, it can be inferred that menthol acts on many different receptors, including cold, warm, pain and taste receptors. However, it is not readily discernible how to isolate which receptor activities would result in a specific sensation such as pleasant cooling without the undesirable sensations such as bitterness or irritation. Neither is it apparent how to control the activity of coolants or other sensory agents such that only the desired sensation is elicited from use of a particular sensory agent. As such, the present invention is focused on the addition of specific synthetic derivatives of cyclohexane (described above) to act as sensates to deliver cooling benefit to users during the hair removal process. Additional sensates can be used to further supplement the cooling feel.

A large number of coolant compounds of natural or synthetic origin are known. The most well-known compound is menthol, particularly l-menthol, which is found naturally in peppermint oil, notably of *Mentha arvensis* L and *Mentha viridis* L. Of the isomers of menthol, the l-isomer occurs most widely in nature and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, i.e., some having disagreeable notes described as earthy, camphor, musty. The biggest difference among the isomers is in their cooling potency. L-menthol provides the most potent cooling, i.e., having the lowest cooling threshold of about 800 ppb, i.e., the concentration where the cooling effect could be clearly recognized. At this level, there is no cooling effect for the other isomers. For example, d-neomenthol is reported to have a cooling threshold of about 25,000 ppb and 1-neomenthol about 3,000 ppb. [R. Emberger and R. Hopp, "Synthesis and Sensory Characterization of Menthol Enantiomers and Their Derivatives for the Use in Nature Identical Peppermint Oils," Specialty Chemicals (1987), 7(3), 193-201]. This study demonstrated the outstanding sensory properties of l-menthol in terms or cooling and freshness and the influence of stereochemistry on the activity of these molecules.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-p-menthan-3-carboxamide, known commercially as "WS-3", and others in the series such as WS-5 (N-ethoxycarbonylmethyl-ρ-menthan-3-carboxamide), and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. TK-10 is described in U.S. Pat. No. 4,459,425 to Amano et al. Other alcohol and ether derivatives of menthol are described e.g., in GB 1,315,626 and in U.S. Pat. Nos. 4,029,759; 5,608,119; and 6,956,139. WS-3 and other carboxamide cooling agents are described for example in U.S. Pat. Nos. 4,136,163; 4,150,052; 4,153,679; 4,157,384; 4,178,459 and 4,230,688.

Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)$_p$-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,111,127; 3,917,613; 3,991,178; 5,5703,123; 5,725,865; 5,843,466; 6,365,215; 6,451,844; and 6,884,903. Ketal derivatives are described, e.g., in U.S. Pat. Nos. 5,266,592; 5,977,166 and 5,451,404.

Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3 (2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., *J. Pharm. Pharmacol.* (1983), 35:110-112. Reviews on the coolant activity of menthol and synthetic coolants include H. R. Watson, et al. *J. Soc. Cosmet. Chem.* (1978), 29, 185-200 and R. Eccles, *J. Pharm. Pharmacol.*, (1994), 46, 618-630.

III. Encapsulated Actives

In one embodiment, the skin engaging member of the present invention further comprises at least one encapsulated active. The encapsulated active can be a thermally resilient skin care active or another skin care composition, such as a cooling agent. In one embodiment, the level of said at least one encapsulated active (including the weight of the capsule and encapsulated active) is from about 0.01% to about 50% by weight of said skin engaging member, alternatively from about 10% to about 45%, alternatively from about 15% to about 35%. The encapsulated actives can contain the same ingredients or different ingredients. The encapsulated actives can also include mixtures of ingredients.

The encapsulated can be a cyclodextrin inclusion complex such as described in U.S. Pat. Nos. 5,653,971, and, 5,713,131 and/or another encapsulation technology. The thermally resilient skin care agents of the present invention can be included as a neat ingredient (as a direct addition into the composition) and/or in an encapsulate. In one embodiment, one of the thermally resilient skin care actives can be in a neat form and another thermally resilient skin care active can be in a capsule.

In one embodiment, encapsulated active comprises more than one cooling agent, for example L-menthol+Menthyl lactate (Frescolat ML); L-menthol+Menthone Glycerine Acetal (Frescolat MGA); or L-menthol+Coolact 10. In yet another embodiment, the encapsulated active comprises at least one cooling agent and a fragrance, a mineral oil, or a combination thereof. In another embodiment, the cooling agent comprises a mixture of menthol and menthyl lactate, such as described in WO 2007115593 (commercially available as Frescolat Plus), or the eutectic mixture of menthol and menthyl lactate in a ratio of weight in the range of 1:4 to 4:1, as described in U.S. Pat. No. 6,897,195.

Suitable cooling agents which can be utilized include non-volatile menthol analogs such as menthyl lactate, menthyl ethoxyacetate, menthone glycerinacetal, 3-1menthoxypropane-1,2-diol, ethyl 1-menthyl carbonate, (IS,3S,4R)-p-menth-8-en-3-ol, menthyl pyrrolidone 25 carboxylate, N-substituted-p-menthane-3-carboxamides (as described in U.S. Pat. No. 4,136,163, which is incorporated herein by reference) including, for example, N-ethyl-pmenthane-3-carboxamide, acyclic carboxamides.

Suitable skin-soothing agents which can be utilized in the cyclodextrin inclusion complex include menthol, camphor, eugenol, eucalyptol, safrol, methyl salicylate, and the afore described menthol analogs. Any suitable cyclodextrin may be utilized to form the inclusion complex including alphacyclodextrin, beta-cyclodextrin, gamma-cyclodextrin and modified cyclodextrins such as hydroxypropyl-beta-cyclodextrin, methyl-beta-cyclodextrin., and acetyl-betacyclodextrin. The preferred cyclodextrins are betacyclodextrin and gamma-cyclodextrin.

When the matrix material comprises a cyclodextrin inclusion complex, the matrix material may also advantageously comprise up to about 10%, preferably about 2 to 7%, by weight of a displacing agent which displaces the skin-soothing agent from the inclusion complex upon contact with water, thereby enhancing the release of the skin-soothing agent from the skin engaging member material during use. The displacing agent is a material which is capable of forming a more stable complex with the cyclodextrin than the complex formed with the skinsoothing agent and, thus, displaces the skin-soothing agent from the complex when the skin engaging member is contacted with water. Suitable displacing agents include surfactants, benzoic acids, and certain amines (e.g. urea). Further details with respect to the aforementioned cooling agents, cyclodextrin inclusion complexes and displacing agents may be found in U.S. Pat. Nos. 5,653,971, and, 5,713,131.

Nonlimiting examples of encapsulation technology other than cyclodextrin complexes include the nano and micro particles described in U.S. Pat. No. 7,115,282. The nano-particles of the present invention are hydrophobic in nature. In one embodiment, the nano-particles have an average diameter in the range from about 0.01 micron to about 10 microns, or from about 0.05 microns to about 5 microns, or from about 0.1 microns to about 2 microns. This linear dimension for any individual particle represents the length of the longest straight line joining two points on the surface of the particle. In one embodiment, a portion of the nano-particles are encapsulated into one or more water-sensitive micro-particles. In one embodiment, the majority of the nano-particles present in the skin engaging member are encapsulated into said water-sensitive micro-particles. The micro-particles have an average particle size of from about 2.0 microns to about 100 microns, or from 20 microns to about 100 microns.

In one embodiment the level of active or actives in the encapsulated active ranges from about 20 to about 90%, preferably from about 30% to about 75% by weight of the nano-particles. In one embodiment the level of the active or actives in the encapsulated active ranges from about 10% to about 60%, or from about 30% to about 50% by weight of the micro-particles. Lower levels of the encapsulated active can also be used, such as low as 10%, or as low as 5%, or as low as 1%.

IV. Hair Removal Head

The hair removal device generally comprises a hair removal head and a handle or grip portion, upon which the hair removal head is mounted. The hair removal device can be a manual or power driven and can be used for wet and/or dry application. The hair removal head can include a wide scraping surface such as where the hair removal device is used with a depilatory, or a razor cartridge where the device is a shaving razor. The hair removal head may be replaceable or pivotally connected to a cartridge connecting structure. In an aspect, the cartridge connecting structure includes at least one arm to releasably engage the hair removal head.

The hair removal head comprises one or more elongated edges positioned between said first and said second end, said one or more elongated edges comprising a tip extending towards said first end. Where the hair removal head is a razor cartridge the one or more elongated edges can include blades. For example, U.S. Pat. No. 7,168,173 generally describes a Fusion® razor that is commercially available from The Gillette Company which includes a razor cartridge with multiple blades. Additionally, the razor cartridge may include a guard as well as a skin engaging member. A variety of razor cartridges can be used in accordance with the present invention. Non-limiting examples of suitable razor cartridges, with and without fins, guards, and/or shave aids, include those marketed by The Gillette Company under the Fusion®, Venus® product lines as well as those disclosed in U.S. Pat. Nos. 7,197,825, 6,449,849, 6,442,839, 6,301,785, 6,298,558; 6,161,288, and U.S. Patent Publ. 2008/060201. Those of skill in the art will understand that the present skin engaging member can be used with any currently marketed system or disposable razor, including those having 1, 2, 3, 4 or 5 blades. Another example of a hair removal device is a scraping edge for use with a hair removal composition, i.e. a depilatory.

In one embodiment, said at least one skin engaging member is located on the portion of the cartridge that contacts skin during the hair removal process, forward and/or aft of the blades. A feature "forward" of the one or more elongated edges, for example, is positioned so that the surface to be treated with by the hair removal device encounters the feature before it encounters the elongated edges. A feature "aft" of the elongated edge is positioned so that the surface to be treated by the hair removal device encounters the feature after it encounters the elongated edges. Where more than one skin engaging member is provided on the hair removal device, they can be the same or different. By different, meaning having a different carrier, a different skin engaging member, or wherein both sheath and composition are different. In one embodiment, where multiple skin engaging members are present on the cartridge, at least one of the skin engaging members is a skin engaging member of the present invention, this skin engaging member can be the one forward or aft of the blades. In another embodiment, both skin engaging members are within the scope of the present invention.

In one embodiment, the cartridge comprises a guard comprising at least one elongated flexible protrusion to engage a user's skin. In one embodiment, at least one flexible protrusion comprises flexible fins generally parallel to said one or more elongated edges. In another embodiment, said at least one flexible protrusion comprises flexible fins, said flexible fins comprising at least one portion which is not generally parallel to said one or more elongated edges. Non-limiting examples of suitable guards include those used in current razor blades and include those disclosed in U.S. Pat. Nos. 7,607,230 and 7,024,776; (disclosing elastomeric/ flexible fin bars); 2008/0034590 (disclosing curved guard fins); 2009/0049695A1 (disclosing an elastomeric guard forming at least one passage extending between an upper surface and a lower surface). In one embodiment, said skin engaging member is positioned on the cartridge aft of the guard and forward of said elongated edge. In another embodiment, the skin engaging member is positioned on the cartridge forward of the guard. This embodiment can be particularly useful to deliver the skin engaging member prior to contact with the guard.

V. Method of Making

Skin engaging member of the present invention is made by extrusion or another high temperature processing, such as injection molding, compression molding, compacting, ultrasonic or radio frequency sintering, and slot coating. High temperature processing degrades/decomposes the water soluble polymers (PEO) as well as the additional benefit ingredients. In one embodiment with EVA grade Elvax 660 (purchased from Dupont) in the shaving aid, the extrusion process temperature is lowered to 110° C. In one embodiment, the skin engaging member comprising the thermally resilient skin care active can further be coated or layered with another shaving aid. In one embodiment, all of the components of the strip, including the high mol wt PEO and low mol wt PEO mixture can be blended alone or in combination with other ingredients prior to molding or extrusion. It can be preferred that the components are free flowing powders, however, liquid skin actives may be adsorbed onto one or more of the other components in the skin engaging member that are in powder form.

In one embodiment, the process of forming a skin engaging member comprises the step of: providing a high mol wt and a low mol wt PEO feed comprising: from about 60% to about 95% by weight of the PEO feed of a high mol wt PEO; and from about 5% to about 30% by weight of the PEO feed of a low mol wt PEO. EVA is included as an additional polymer, and other ingredients can also be included with the PEO feed or before or after this PEO feed. Those of skill will understand that if additional PEOs (which do not qualify as high or low mol wt PEO) are included in this feed, these other PEOs would not be counted as a portion of the high mol wt and low mol wt PEO feed.

The PEO feed can be combined with a second feed if additional ingredients are desired. The feed or feeds can be mixed and processed through a step of extrusion through a die to form a shaving aid suitable for use as a skin engaging member. As will be explained below, said step of extruding can include subjecting said mixture to a pressure of from about 1000 psi to about 7500 psi and/or a temperature of from about 100° C. to about 160° C.

The blended components may be extruded through a Rondol 18, 18 mm diameter extruder with a barrel pressure of about 500-1000 psi, a rotor speed of about 10 to 50 rpm, and a temperature of about 100°-160° C. and a die temperature of about 100°-160° C. Alternatively, a 1½ inch single screw extruder may be employed with a processing temperature of 100°-160° C., preferably 110-130° C., a screw speed of 20 to 50 rpm, preferably 25 to 50 rpm, and an extrusion pressure of 1800 to 7500 psi, preferably 4000 to 6500 psi. Other extrusion conditions can also be employed. The extruded strip is cooled to about 25° C. To injection mold the strips it is preferred to first extrude the powder blend into pellets. This can be done on a 1¼ or 1½ inch single screw extruder at a temperature of 100°-140° C., preferably 110°-130° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 100° to 185° C., preferably from 110° to 145° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds. In one embodiment, one or more feeds can be preheated or they can be fed in at ambient temperature.

In one embodiment, the process further comprises a step of providing a skin engaging member receiving region (such as a portion of a first layer or base or sheath) and distributing a volume of the PEO feed into said skin engaging member receiving region (to form a second layer or core). Where a sheath and core system are used, the sheath can be performed by molding and the core can be thereafter formed within the sheath by providing said PEO mixture in a fluid or flowable form (such as a liquid or powder) then solidifying it such as by pressurizing, heating and or ultrasonically compressing said PEO feed within said skin engaging member receiving region. Non-limiting examples of ways to form such skin engaging members are disclosed in U.S. Pat. No. 6,298,558 or 7,581,318 as well as WO 2011/047221.

VI. Details on Figures

Figure 1:
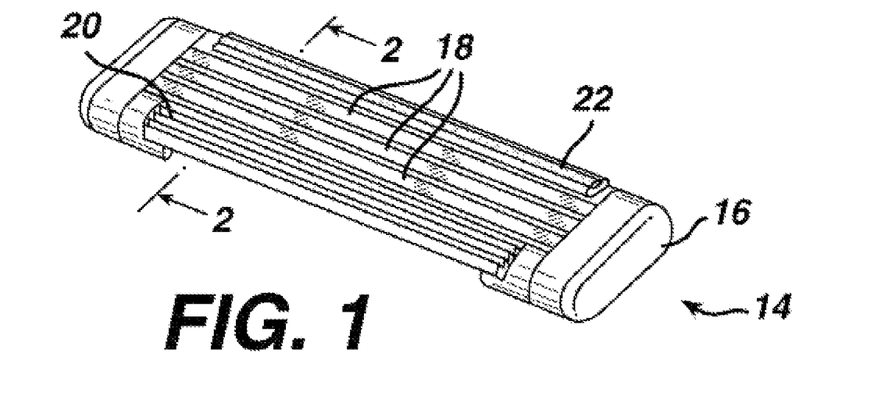
FIG. 1 is a perspective view of a razor cartridge which includes a skin engaging member of the present invention.
Figure 3:
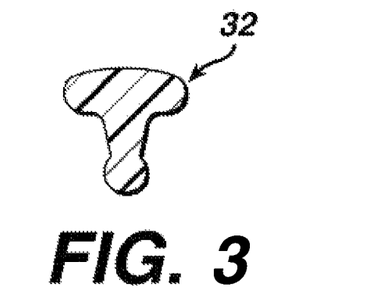
FIG. 3 is a side elevation view of second type of skin engaging member of the present invention.

Referring to FIGS. 1 and 2, the razor cartridge 14 includes housing 16, which carries three blades 18, a finned elastomeric guard 20, and a skin engaging member 22 located on a skin-engaging portion (in this case the cap) of the cartridge. Skin engaging member 22 is shown having two layers, the first layer can be the matrix and encapsulated active of the present invention, and the second layer can be a conventional shave aid, or vice versa. The skin engaging member is preferably locked in (via adhesive, a fitment, or melt bonding) an opening or on a plate or other flat surface in the rear of the cartridge. Skin engaging member 32, shown in FIG. 3, is similar to skin engaging member 22, except that skin engaging member 32 has a homogeneous composition throughout and a uniform, slightly curved to flat upper surface.

VII. Examples

The following examples are made in accordance with the present invention, all amounts are in wt %. These examples can be processed via extrusion with a profile die at an extrusion temperature of 120° C. Adjunct components commonly used in extruded skin engaging members are added to bring the total formulation to 100%.

Example 1

| Material | Example 1 | Example 2 | Example 3 |
|---|---|---|---|
| Dow Polyox N-750 | 26.87 | 0 | 29.16 |
| Dow Polyox Coagulant | 41.14 | 63.01 | 44.69 |
| Carbowax 4600 PEG | 5.00 | 5.00 | 5.00 |
| Irganox Antioxidant | 0.25 | 0.25 | 0.25 |
| EVA | 26.74 | 31.74 | 15.95 |

A skin engaging member can be made in accordance with any of Example 1, Example 2, or a mixture thereof in a single layer. In another embodiment, a different composition (Example 3) can be used as a top layer and either Example 1 or 2 can be a layer on said base. In another embodiment, multiple layers in accordance with the present invention can be coated on said base made of Example 3. In another embodiment, a composition in accordance with the present invention can be used as the base, and a composition such as Example 3 can be used as the layer on the base. In one example, the skin engaging member comprises a top layer of Example 3, and a base layer of Examples 1 or 2. Elvax 660 (12% Vinyl Acetate by Weight) EVA grade is used and the additional polymer.

Additional examples made in accordance with one or more embodiments of the present invention include the following.

|  | Example 4 | Example 5 | Example 6 |
|---|---|---|---|
| Polyox | 50% | 50% | 59% |
| EVA with 12% VA | 27% | 27% | 27% |
| EVA with 18% VA | 0% | 10% | 0% |
| HIPS | 0% | 0% | 0% |
| Polycaprolactone | 5% | 5% | 5% |

|  | Example 7 | Example 8 | Example 9 | Example 10 |
|---|---|---|---|---|
| Polyox | 64% | 64% | 59% | 54% |
| EVA with 12% VA | 27% | 27% | 32% | 0% |
| EVA with 18% VA | 0% | 5% | 0% | 40% |
| HIPS | 0% | 5% | 0% | 0% |
| Polycarpolactone | 0% | 5% | 0% | 0% |

Examples 4-10 are extruded in a single die extruder at a temperature between 110° C. and 130° C. Polyox can be a blend of N750 and coagulant as used in Examples 1-3, or can be one of these grades of polyox.

|  | Example 11 | Example 12 | Example 13 | Example 14 |
|---|---|---|---|---|
| PEO | 64% | 54% | 59% | 59% |
| EVA with 2.5% VA | 0 | 0 | 0 | 5% |
| EVA with 9% VA | 0 | 0 | 27% | 22% |
| EVA with 12% VA | 27% | 0% | 0% | 0% |
| EVA with 18% VA | 0% | 40% | 0% | 0 |
| HIPS | 0% | 0% | 0% | 0 |
| Polycaprolactone | 0% | 5% | 5% | 0% |

|  | Example 15 | Example 16 | Example 17 | Example 18 |
| --- | --- | --- | --- | --- |
| PEO | 51% | 59% | 64% | 59% |
| EVA with 2.5% VA | 0% | 27% | 0% | 0 |
| EVA with 4% VA | 0% | 0% | 27% | 0% |
| EVA with 9% VA | 35% | 0% | 0% | 26% |
| EVA with 12% VA | 0% | 0% | 0% | 0% |
| HIPS | 0% | 0% | 0% | 1% |
| Polycaprolactone | 5% | 5% | 0% | 5% |

Each of Examples 4-18 is believed to be within the scope of the present invention and thus provides lubrication after 8 shaves and also retains mechanical integrity after 8 shaves. Panel testing is conducted on Examples 11-13 and 15 with results confirming that lubrication and mechanical integrity were maintained after 8 shaves. This testing includes the following test design:

10 total panelists are obtained (5 per leg).

Each leg participates in a split face shave test with a control (Mach 3 Turbo razor) vs experimental (same razor cartridge but with an experimental skin engaging member).

Participants will shave as needed according to normal shave habits (same frequency, same prep usage etc) for 3 weeks.

Panelists are asked to report any major mechanical defect issues experienced during shaving.

Similar testing can be conducted with other additional measurements such as:

After the shave study, cartridges are inspected by trained inspector against a visual grading scale. Inspector trained to detect skin engaging members that are significantly curled out of the housing with a large gap between the insert and the frame and/or In a Soak Dry lab method: skin engaging members are snapped into housings and soaked in water for a few minutes; then dried. This is repeated for multiple soak-dry cycles, after which images are captured of the skin engaging members and they are visually inspected against a numerical grading scale.

|  | Example A | Example B | Example C |
| --- | --- | --- | --- |
| Polyox (Coag) | 48% | 0% | 0% |
| Polyox (N750) | 32% | 37.2% | 0% |
| Polyox (WSR 308) | 0% | 24.8% | 70% |
| EVA with 18% VA | 0% | 0% | 24% |
| EVA with 25% VA | 20 | 0% | 0% |
| EVA with 32% VA | 0% | 32% | 0% |
| Total % VA | 5% | 11.2 | 4.32 |
| Retains mechanical integrity after 8 shaves | NO | NO | YES |

Comparative Examples A-C show how different formulations with varying grades of EVA can be within or outside the scope of invention.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the DETAILED DESCRIPTION OF THE INVENTION are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern. Except as otherwise noted, the articles "a," "an," and "the" mean "one or more."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair removal device comprising at least one blade, and a skin engaging member comprising:
   a. about 51% to about 70% of a polyethylene oxide by weight of the skin engaging member; and
   b. about 22% to about 40% of an ethylene vinyl acetate by weight of the skin engaging member, said ethylene vinyl acetate having a vinyl acetate % of about 18 or less, wherein said ethylene vinyl acetate is selected from the group consisting of:
      i. an ethylene vinyl acetate having 18% vinyl acetate, and the skin engaging member has a total vinyl acetate level of from about 4% to about 7.2%, by weight of the skin engaging member;
      ii. an ethylene vinyl acetate having 12% vinyl acetate, and the skin engaging member has a total vinyl acetate level of from about 2.6% to about 4.8%, by weight of the skin engaging member;
      iii. an ethylene vinyl acetate having 9% vinyl acetate, and the skin engaging member has a total vinyl acetate level of from about 2.0% to about 3.6%, by weight of the skin engaging member;
      iv. an ethylene vinyl acetate having 2.5% vinyl acetate, and the skin engaging member has a total vinyl acetate level of from about 0.55% to about 1%, by weight of the skin engaging member; and
      v. a mixture thereof.

2. The hair removal device of claim 1, further comprising at least one of polyethylene, polypropylene, polystyrene, butadiene-styrene copolymer, polyacetal, acrylonitrile-butadiene-styrene copolymer, polyurethane, or blends thereof.

3. The hair removal device of claim 1, wherein said vinyl acetate % is not determined on an as added basis.

4. The hair removal device of claim 1, further comprising a skin care active.

5. The hair removal device of claim 1, further comprising an encapsulated active.

6. A process of forming a skin engaging member of claim 1 comprising:
   1. providing a polyethylene oxide;
   2. providing ethylene vinyl acetate having a vinyl acetate % of 18% or less;
   3. forming a matrix from said polyethylene oxide and ethylene vinyl acetate;
   4. extruding said matrix into a skin engaging member comprising:
      a. about 51% to about 70% of a polyethylene oxide by weight of the skin engaging member; and
      b. about 22% to about 40% of an ethylene vinyl acetate by weight of the skin engaging member, said ethylene vinyl acetate having a vinyl acetate % of about 18 or less, wherein said ethylene vinyl acetate is selected from the group consisting of:
         i. an ethylene vinyl acetate having 18% vinyl acetate, and the skin engaging member has a total vinyl acetate level of from about 4% to about 7.2%, by weight of the skin engaging member;
         ii. an ethylene vinyl acetate having 12% vinyl acetate, and the skin engaging member has a total vinyl acetate level of from about 2.6% to about 4.8%, by weight of the skin engaging member;
         iii. an ethylene vinyl acetate having 9% vinyl acetate, and the skin engaging member has a total vinyl acetate level of from about 2.0% to about 3.6%, by weight of the skin engaging member;
         iv. an ethylene vinyl acetate having 2.5% vinyl acetate, and the skin engaging member has a total vinyl acetate level of from about 0.55% to about 1%, by weight of the skin engaging member; and
         v. a mixture thereof.

7. The process of claim 6, further comprising a step of extruding said matrix at a process temperature between about 100 to about 160° C.

8. The process of claim 6, further comprising a step of mixing said polyethylene oxide and said ethylene vinyl acetate prior to forming said mixture.

9. The process of claim 6, further comprising a step of providing a skin care active to be included into said matrix.

10. The process of claim 6, further comprising a step of providing an encapsulated active to be included into said matrix.

11. The process of claim 6, further comprising a step of providing at least one of polyethylene, polypropylene, polystyrene, butadiene-styrene copolymer, polyacetal, acrylonitrile-butadiene-styrene copolymer, polyurethane, or blends thereof, to be included into said matrix.

12. The process of claim 6, wherein said vinyl acetate % is not determined on an as added basis.

* * * * *